(12) United States Patent
Greenblatt et al.

(10) Patent No.: US 6,743,796 B2
(45) Date of Patent: Jun. 1, 2004

(54) PIPERAZINYL-ISATINS

(75) Inventors: Lynne P. Greenblatt, Lambertville, NJ (US); Ivo Jirkovsky, Nanuet, NY (US); Richard E. Mewshaw, King of Prussia, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/139,695

(22) Filed: May 3, 2002

(65) Prior Publication Data

US 2003/0013722 A1 Jan. 16, 2003

Related U.S. Application Data

(60) Provisional application No. 60/289,171, filed on May 7, 2001.

(51) Int. Cl.[7] ............... A61K 31/496; C07D 403/00
(52) U.S. Cl. ............... 514/254.09; 544/373; 544/392
(58) Field of Search ................ 544/373; 514/254.09

(56) References Cited

U.S. PATENT DOCUMENTS 4,593,106 A  6/1986 Stringer et al.

FOREIGN PATENT DOCUMENTS

| EP | 0 189 612 A1 | 8/1986 |
|---|---|---|
| EP | 138 280 | 6/1988 |
| EP | 0 189 612 B1 | 11/1992 |
| WO | WO 94/13659 | 6/1994 |
| WO | WO 94/15919 | 7/1994 |
| WO | WO 94/21610 | 9/1994 |
| WO | 98/27081 | 6/1998 |
| WO | 00/29397 | 5/2000 |
| WO | 00/78728 | 12/2000 |

OTHER PUBLICATIONS

Bioorg. & Med. Lett. 8, 2675–2680, 1998, New Generation of Dopaminergic Agents. 5, Heterocyclic Bioisosteres that Exploit the 3–OH–N[1]–Phenylpiperzine Dopaminergic Template, Mewshaw et al.

Helv. Chim. Acta 40(No. 31), 249–255, 1979, La réactivitié du groupement crabonyle et l'activité déshydrogenasique des composés de la série de l'isatine, Giovannini et al.

J. Org. Chem. 44, 237–239, 1979, Metalation of Aromatic Tertiary Diamines with n–Butyllithium, Friedmann et al.

J. Org. Chem. 44, 1133–1136, 197, Ortho Functionalization of Aromatic Amines: Ortho Lithiation of N–Pivaloylanilines, Fuhrer et al.

Tet. Lett. 35, 7303–7306, 1994, A General Method for the Synthesis of Isatins: Preparation of Regiospecifically Functionalized Isatins from Anilines, Hewawasam et al.

Lect. Heterocyclic Chem. 7, 95–106, 1984, New Directions in Heterocyclic Synthesis Using Metalated Benzamides, Victor Snieckus.

J. Med. Chem. 36, 2716–2725, 1993, Preparation of Substituetd N–Phenyl–4–aryl–2–pyrimidinamines as Mediator Release Inhibitors, Paul et al.

*Primary Examiner*—Emily Bernhardt
(74) *Attorney, Agent, or Firm*—Joseph Mazzarese; Kimberly R. Hild

(57) ABSTRACT

This invention provides compounds of formula VI

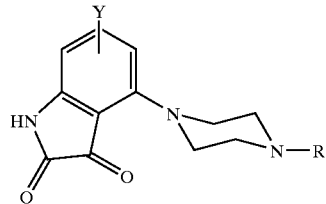

VI wherein

Y is hydrogen, methyl, methoxy, methylthio or trifluoromethyl;

R is hydrogen, $C_{1-3}$alkyl or $(CH_2)_n Ar$;

n is 0, 1 or 2; and

Ar is phenyl or methoxyphenyl, or a pharmaceutically acceptable salt thereof. These compounds are selective dopamine autoreceptor agonists useful in treating disease states involving hyperactivity of dopamine systems. The invention also comprises intermediate compounds, compositions and methods related to the compounds of formula VI.

11 Claims, No Drawings

PIPERAZINYL-ISATINS

This application claims priority from copending provisional application serial No. 60/289,171 filed on May 7, 2001, the entire disclosure of which is hereby incorporated by reference.

BACKGROUND OF THE INVENTION

This invention relates to the field of dopamine receptor partial agonists, and in particular to novel 4-piperazinyl-isatins, their preparation, and their therapeutic use, e.g., in the treatment of psychosis.

Dopamine antagonists have been used for years in the treatment of disorders of the dopaminergic system, such as schizophrenia. These antagonists block the $D_2$ receptors. Unfortunately, this causes undesirable side effects. Dopamine autoreceptor agonists, including partial agonists, can be used to induce antipsychotic activity without causing the same side effects as antagonists.

Intrinsic activity at the dopamine $D_2$ receptor may be predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, and these activities characterize a compound's ability to elicit an antipsychotic effect.

WO 94 13659 discloses fused benzo compounds of the general Formula I

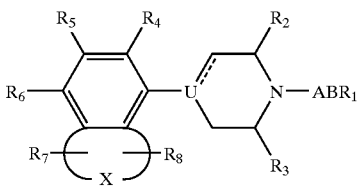

wherein X is selected from a broad base of divalent 3–4 membered groups, including the possibility of forming imidazoles, which potently bind to the 5-$HT_{1A}$ receptor and have central serotonergic 5$HT_{1A}$ activity for the treatment of certain psychic and neurological disorders.

EP 0138280 discloses piperazinyl compounds of Formula II having a bicyclic heteroaryl radical in the 4-position and a heteroaryl-, aryl-, or alkyl substituted carbamoylethyl or carbamoylpropyl in the 1-position. These compounds are alleged to show blood pressure lowering effect through a central mechanism. When n=1, the compounds are piperazines.

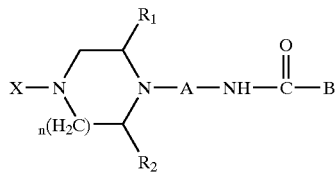

WO 94 15919 (Formula III) and WO 94 21610 (Formula IV) disclose piperazine derivatives which act on the central nervous system by binding to 5-HT receptors, particularly 5-$HT_{1A}$ type, for the use in the treatment of CNS disorders, such as anxiety, depression, and cognition disorders. In both Formula III and Formula IV, Z and $R_1$ refer to heteroaryl groups.

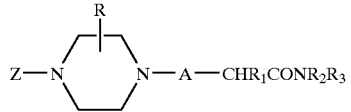

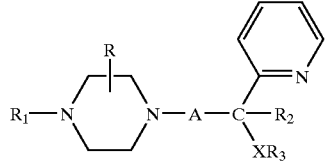

R. E. Mewshaw et al (*Bioorg. & Med. Chem. Lett.* 8, 2675–2680, 1998) describe heteroarylpiperazines of Formula V which have excellent affinity for the $D_2$ receptor, and are potentially useful as antipsychotic agents.

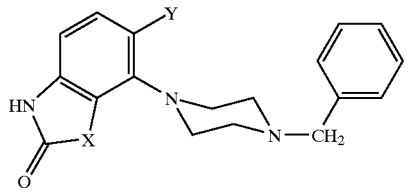

E. Giovannini et al. (*Helv. Chim. Acta* 40, 249, 1957) reported that 4-amino-isatin had been prepared.

Several techniques useful for forming derivatives are known in the art. G. Friedmann et al. (*J. Org. Chem.* 44, 237, 1979) described lithiation of N,N,N',N'-tertramethyl-ortho- and para-phenylenediamine. An improvement was revealed by W. Fuhrer and H. W. Gschwend (*J. Org. Chem.* 44, 1133, 1979) which involved a combined ortho-directing effect as illustrated by lithiation of N-pivaloyl-3-methoxyaniline. P. Hewawasam and N. A. Meanwell (*Tetrahedron Letters*, 3, 7303, 1994) disclosed the conversion of several 3-(suitably substituted) anilines into corresponding 2-(α-ketoesters) by means of diethyl oxalate; subsequent hydrolytic deprotection produced substituted isatins. However, the literature does not disclose the analogous lithiation of metaphenylenediamine derivatives, such as 3-(4'-R-piperazin-1'-yl) anilines. The choice of the directing and protecting groups appears to be of critical importance in lithiating different species, and such choice is by no means obvious, as is indicated by the disclosures of P. Hewawasam and N. A. Meanwell (*Tetrahedron Letters*, 35, 7303, 1994) and V. Snieckus, *Lect. Heterocylic Chem.*, 95–106, 1984).

SUMMARY OF THE INVENTION

The present invention comprises novel 4-piperazinyl compounds of Formula VI

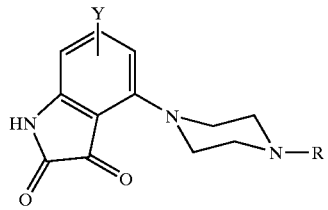

wherein
- Y is hydrogen, methyl, methoxy, methylthio, or trifluoromethyl;
- R is H, $C_{1-3}$alkyl, or $(CH_2)_nAr$;
- n is 0, 1, or 2; and
- Ar is phenyl or methoxyphenyl, and pharmaceutically acceptable salts thereof.

The present invention further comprises compounds of Formula VII and Formula VIII

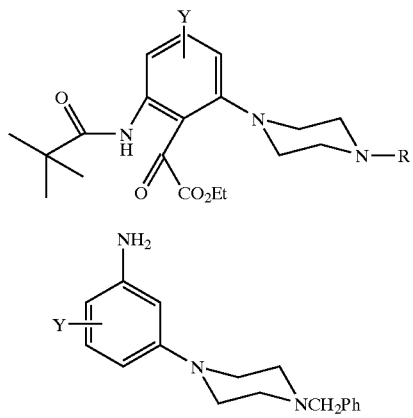

which are useful in making compounds of Formula VI, wherein Y and R have the same definition as in Formula VI. Ph represents a phenyl group and Et represents an ethyl group.

The present invention also includes compositions containing Formula VI compounds; methods for making compounds of Formula VI and Formula VII; and methods of treatment comprising administering a compound of Formula VI or a pharmaceutically acceptable salt thereof to a mammal to reduce dopamine synthesis, and/or to treat disorders of the dopaminergic system, such as schizophrenia, Parkinson's disease, hyperprolactinemia, depression, and Tourette's syndrome. Preferably, the compounds of the invention are those wherein R' is a hydrogen atom and R is not a hydrogen atom; such compounds wherein Ar is phenyl, n is 1, and Y is hydrogen are more preferred.

DESCRIPTION OF INVENTION

This invention comprises novel isatins substituted in position 4 with a tertiary amino group, preferably 4-(4'-R-piperazin-1'-yl)isatins, where R is H, alkyl, or aralkyl. One highly preferred embodiment of the invention is 4-(4'-benzylpiperazin-1'-yl)isatin.

The 4-piperazinylisatins of this invention have biological activity as an antipsychotic agent. These compounds are essentially free from extrapyramidal side effects (EPS). The compounds of this invention are selective autoreceptor agonists, functioning primarily to activate only autoreceptors versus postsynaptic $D_2$ dopamine receptors. As such, they provide functional modulation of dopamine systems of the brain without the excessive blockade of the postsynaptic dopamine receptors, which have been observed to be responsible for the serious side effects frequently exhibited by agents found otherwise clinically effective for treatment of schizophrenia. Activation of the dopamine autoreceptors results in reduced neuronal firing as well as inhibition of dopamine synthesis and release and therefore provide a means of controlling hyperactivity of the dopaminergic systems.

More specifically, the compounds of this invention comprise those depicted by the following Formula VI:

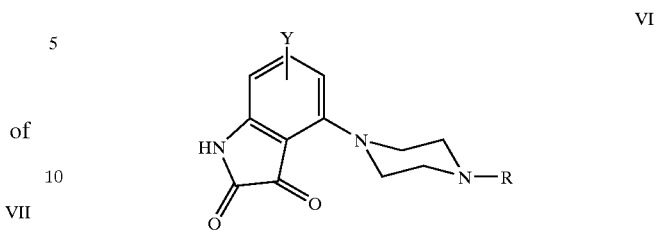

wherein
- Y is hydrogen, methyl, methoxy, methylthio, or trifluoromethyl;
- R is H, $C_{1-3}$alkyl, or $(CH_2)_nAr$;
- n is 0, 1, or 2; and
- Ar is phenyl or methoxyphenyl, and pharmaceutically acceptable salts thereof.

Those skilled in the art will be readily able to determine which salts of the compounds of this invention are pharmaceutically acceptable. The pharmaceutically acceptable salts of the compounds of this invention include those derived from such organic and inorganic acids, such as: acetic, lactic, citric, fumaric, tartaric, succinic, maleic, malonic, oxalic, hydrochloric, hydrobromic, phosphoric, nitric, sulfuric, methanesulfonic, methylbenzene sulfonic, and similarly known acceptable acids.

The term alkyl as used herein includes both straight chain and branched moieties.

A preferred embodiment of this invention is compounds of formula VI wherein Y is hydrogen, methyl, methoxy at the 5 or 7 position, methylthio at the 7 position, or trifluoromethyl at the 5 or 6 position, and R is $(CH_2)Ar$. Highly preferred compounds of this invention include those compounds of Formula VI in which Y=H, n=1 and Ar=phenyl.

The compounds of this invention can be prepared from starting materials that are either commercially available or can be prepared by standard procedures known to those skilled in the art. The compounds of Formula VI can be generally prepared as shown in Reaction Scheme I, which specifically illustrates the reaction scheme for making 4-(4-benzyl-piperazin-1-yl)-1H-indole-2.3-dione.

Reaction Scheme I

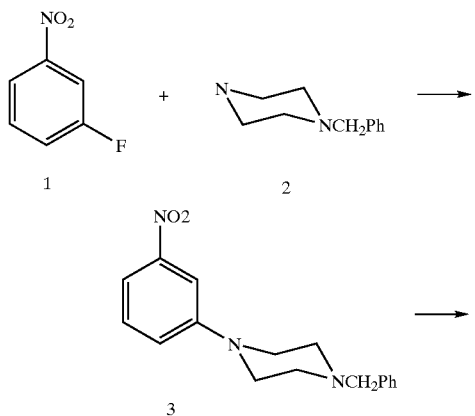

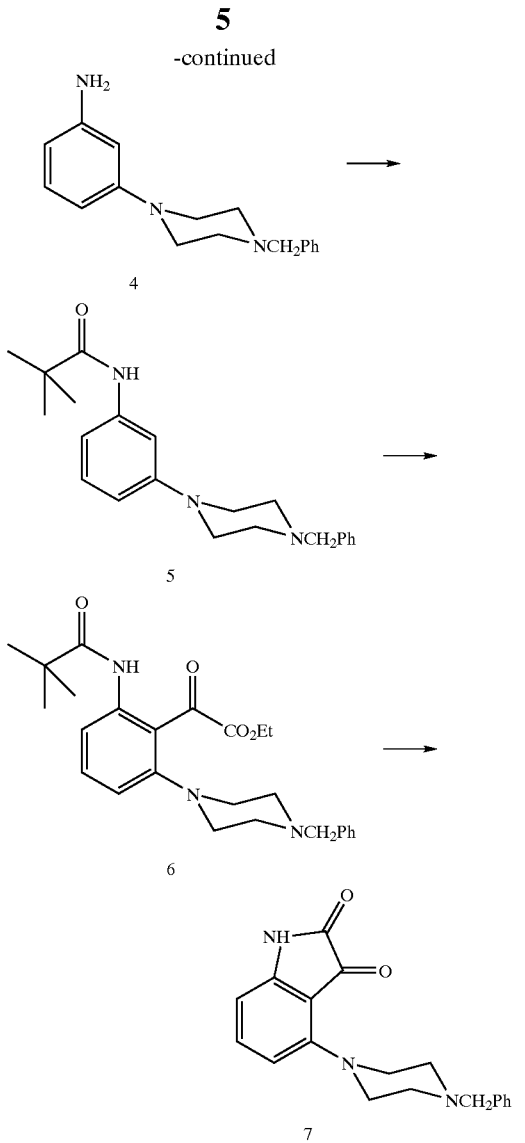

Compound 7 may be useful in the preparation of more substituted isatins, for example by substitution on the isatin nitrogen, or removal of the piperazinyl benzyl group and subsequent substitution with alkyl or aralkyl groups.

Other compounds of this invention wherein Y is not H may be prepared in a manner analogous to Reaction Scheme I. Illustrative examples of these compounds are presented in the table below, which shows the derivatives of compound 7 that will be formed according to Reaction Scheme 1 starting with a specified compound 1:

| Compound 1 | Compounds 6 and 7 |
|---|---|
| 2-fluoro-4-nitrotoluene | 5-methyl derivative |
| 3-fluoro-5-nitrotoluene | 6-methyl derivative |
| 4-fluoro-2-nitrotoluene | 7-methyl derivative |
| 2-fluoro-1-methoxy-4-nitrobenzene | 5-methoxy derivative |
| 4-fluoro-1-methoxy-2-nitrobenzene | 7-methoxy derivative |
| 4-fluoro-1-methylthio-2-nitrobenzene | 7-methylthio derivative |
| 2-fluoro-4-nitro-1-trifluoromethylbenzene | 5-trifluoromethyl derivative |
| 1-fluoro-3-nitro-5-trifluoromethylbenzene | 6-trifluoromethyl derivative |

Other examples will be readily apparent to those skilled in the art.

The present invention discloses a useful approach to derivatives of 4-amino-isatins and, as specifically defined in Reaction Scheme I, to 4-(4'-benzylpiperazin-1-yl)isatin. The synthetic methodology involves regiospecific, ortho-directed lithiation of N-[3-(4'-benzylpiperazin-1'-yl) phenyl]-2,2-dimethylpropionamide (i.e., pivaloylamide), followed by treatment of the metalated species with diethyl oxalate, and ring closure. The choice of directing and protecting groups appears to be of critical importance in lithiating different species.

The starting material of the present invention, 1-(3-nitrophenyl)-4-benzylpiperazine, is prepared by condensation of benzylpiperazine with 1-fluoro-3-nitrobenzene in the same fashion as described by H. Kotsuki et al (*Synthesis*, 12, 1147–1148, 1990), and R. Paul et al. (*J. Med. Chem.* 36, 2716, 1993) for 1-(3-nitrophenyl)-4-methylpiperazine. The 1-(3-aminophenyl)-4-benzyl-piperazines are novel compounds, useful pharmaceutical intermediates, and potential precursors of other piperazine derivatives.

The compounds of this invention may be administered orally or parenterally, neat or in combination with conventional pharmaceutical carriers. Applicable solid carriers for pharmaceutical compositions containing the compounds of this invention can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is typically mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinyl-pyrrolidone, low melting waxes and ion exchange resins.

Liquid carriers may be used in preparing solutions, suspensions, emulsions, syrups and elixirs containing one or more compounds of the present invention as active ingredient(s). The active ingredient can be dissolved or suspended in a pharmaceutically acceptable liquid carrier such as water, an organic solvent, pharmaceutically acceptable oils or fat, or mixtures of any of these carriers.

The liquid carrier can contain other suitable pharmaceutical additives such as solubilizers, emulsifiers, buffers, preservatives, sweeteners, flavoring agents, suspending agents, thickening agents, coloring agents, viscosity regulators, stabilizers or osmo-regulators. Suitable examples of liquid carriers for oral and parenteral administration include water (particularly containing additives, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil, or arachis oil). For parenteral administration the carrier can also be an oily ester such as ethyl oleate and isopropyl myristate. Sterile liquid carriers are needed for use in sterile liquid compositions for parenteral administration.

Liquid pharmaceutical compositions which are essentially sterile solutions or suspensions can be utilized by, for example, intramuscular, intraperitoneal or subcutaneous injection. Sterile solutions can also be administered intravenously. Oral administration may accomplished using either liquid or solid composition forms.

Preferably the pharmaceutical composition is in unit dosage form, e.g. as tablets or capsules, in which each unit dose contains an appropriate quantity of the active ingredient. The unit dosage forms of compositions according to the present invention can be packaged in any manner acceptable in the art; for example, these compositions may be packaged in packets containing solid forms such as powder, or in vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient. The treatment of substance abuse follows the same method of subjective drug administration under the guidance of the attending physician. Based upon the potency of the compounds of this invention, it is believed that the appropriate dose for a human patient will be from about 5 to about 100 mg/day. Conventionally, such treatments begin with the lower dose with gradual increase at the rate of about 5 mg/day until the desired response pattern is achieved. The optimum human dosage typically is expected to be in the range of about 15 mg/day to about 75 mg/day.

The following Examples illustrate specific embodiments of this invention; however, the scope of this invention is not limited to the embodiments illustrated in these Examples, but encompasses the full scope of the subject matter set forth in the appended claims.

EXAMPLE I

1-Benlyl-4-(3-nitrophenyl)-piperazine

A mixture of 1-benzylpiperazine (8.8 g, 50 mmol), 1-fluoro-3-nitrobenzene (5.3 g, 37.5 mmol) and potassium carbonate (13.8 g, 0.1 mol) in dimethyl sulfoxide (50 mL) was stirred at 100° C. for 24 hrs. The reaction mixture was cooled to room temperature, poured into ice water (150 mL) and extracted with diethyl ether (3×50 mL). The combined organic layers were washed with brine (50 mL), dried over anhydrous magnesium sulfate, filtered, and the solvent removed under vacuum. Purification by chromatography (240 g, silica gel, 2% methanol in chloroform) afforded 5.4 g (48%) as an orange oil, which was analyzed using NMR ($CDCl_3$) spectroscopy; the resulting NMR spectrum contained the following peaks: δ 2.61 (4H, t), δ 3.27 (4H, t), δ 3.56 (2H, s), δ 7.15 (1H, ddd), δ 7.24–7.37 (6H, m), δ 7.62 (1H, ddd), δ 7.68 (1H, t), confirming the presence of 1-benzyl-4-(3-nitrophenyl)-piperazine.

EXAMPLE II 3-(4-Benzyl-piperazin-1-yl)-phenylamin

A mixture of 1-benzyl-4-(3-nitrophenylypiperazine (5.4 g, 18 mmol) and 10% palladium on carbon (500 mg) in ethanol (100 mL) was hydrogenated at ambient temperature and pressure for 4 hours. The catalyst was removed by filtration and rinsed with ethanol, and the filtrate concentrated under vacuum to afford 2.95 g (61%) as a beige solid, which ws analyzed using NMR ($CDCl_3$) spectroscopy; the resulting NMR spectrum contained the following peaks: δ 2.59 (4H, t, J=6 Hz), δ 3.17 (4H, t, J=6 Hz), δ 3.56 (2H, s), δ 6.19 (1H, dd), δ 6.23 (1H, t), δ 6.34 (1H, dd), δ 7.00 (1H, t), δ 7.22–7.36 (5H, m), confirming the presence of 3-(4-benzyl-piperazin-1-yl)-phenylamine.

EXAMPLE III

N-[3-(4-Benzyl-piperazin-1-yl)-phenyl]-2,2-dimethyl-propolnamide

The crude 3-(4-benzyl-piperazin-1-yl)-phenylamine made in Example II (2.95 g, 11 mmol) was dissolved in dichloromethane (100 mL), and a solution of sodium carbonate (3.1 g, 11 mmol) in water (20 mL) was added, and the resulting two phase mixture stirred vigorously while trimethylacetyl chloride (1.3 g, 11 mmol) was added dropwise. Strring was continued at ambient temperature for 30 minutes, layers were separated, and the aqueous layer further extracted with dichloromethane (20 mL). The combined organic layers were washed with brine, dried over anhydrous magnesium sulfate, filtered, and the solvent removed under vacuum to yield 3.84 g of a beige solid foam. Purification by chromatography (150 g silica gel, 4% methanol in chloroform) followed by crystallization from diethyl ether and petroleum ether afforded 2.84 g (74%) of the title compound as a light beige crystalline powder having a melting point of 156–158° C.

The presence of the title compound was confirmed by mass spectrometry, proton NMR (400 MHz, DMSO-d6), infrared spectrometry, and elemental analysis.

Mass Spectroscopy: (+)FAB $[M+H]^+$ @ m/z 352.

Elemental Analysis for: $C_{22}H_{29}N_3O$.

Calculated % (Theoretical): C, 75.18; H, 8.32; N, 11.95.

% Found by Analysis: C, 75.01; H, 8.40; N, 11.76.

EXAMPLE IV

[2-(4-Benzyl-piperazin-1-yl)-6-(2,2-dimethyl-propionylamino)-phenyl]oxo-acetic acid ethyl ester Under a nitrogen atmosphere, a solution of N-[3-(4-benzyl-piperazin-1-yl)-phenyl]-2,2-dimethyl-propionamide (2.4 g, 6.8 mmol) and N,N,N'N'-tetramethylethylenediamine (3.2 g, 27.4 mmol) in tetrahydrofuran (24 mL) was stirred for 15 minutes at 0° C., n-butyllithium (2.5M in hexane) (11 mL, 27.5 mmol) was added dropwise, and the mixture stirred for 3 hours at 15° C. The mixture was then cooled to −78° C., and diethyl oxalate (4.0 g, 27.4 mmol) was added. The mixture was stirred at −20° C. for 30 minutes, poured into a saturated aqueous solution of ammonium chloride (50 mL), and the product extracted into ethyl acetate (3×30 mL). The combined organic layers were washed with brine (20 mL), dried over anhydrous magnesium sulfate, filtered, and the solvent removed under vacuum to yield 4.5 g of crude product as a light brown oil. Purification by chromatography (150 g silica gel, 2% methanol in chloroform) afforded the title compound (1.5 g, 3.3 mmol, 49% yield) as a straw colored oil; this compound was confirmed by the following mass spectrometry results: EI $M^+$ @ m/z 451 and (+)FAB $[M+H]^+$ @ m/z 452, $[M+Na]^+$ @ m/z 474.

EXAMPLE V 4-(4-Benzyl-piperazin-1-yl)-1H-indole-2,3-dione

A mixture of [2-(4-benzyl-piperazin-1-yl-6-(2,2-dimethyl-propionyl-amino)-phenyl]-oxo-acetic acid ethyl ester (900 mg, 2 mmol) and 6N hydrochloric acid (15 mL) was heated to reflux for 2 hours, cooled in an ice bath, rendered basic with sodium bicarbonate, and the product extracted into dichloromethane (2×30 mL). The combined organic layers were dried over anhydrous magnesium sulfate, filtered, and the solvent removed under vacuum to give 600 mg of a dark orange solid foam. Purification by chromatography (40 g silica gel, 1:1 ethyl acetate:chloroform) afforded the title compound (1.3 mmol; 65% yield) as an orange solid foam. An ethanolic solution of the product was treated wit lumaric acid (1 equivalent) to give the monofumarate 0.66 ethanolate salt as an orange solid having a melting point of 118–120° C. The title compound characterized by mass spectrometry, proton NMR (400 MHz, DMSO-d6), Infrared spectrometry, and elemental analysis.

Mass Spectroscopy: EI M+@ m/z 321.

Elemental Analysis for: $C_{19}H_{19}N_3O_2 + 1.0 C_4H_4O_4 + 0.66 C_2H_6O$.

Calculated % (Theoretical): C, 62.44; H, 5.81; N, 8.98.

% Found by Analysis: C, 62.26; H, 5.84; N, 9.36.

The compounds of this invention depicted in formula VI are dopamine autoreceptor agonists, that is, they serve to modulate the synthesis and release of the neurotransmitter dopamine. They are useful for the treatment of disorders of the dopaminergic system, such as schizophrenia, Parkinson's disease, hyperprolactinemia, depression, and Tourette's syndrome. As partial agonists at the postsynaptic dopamine $D_2$ receptor, these compounds are also useful in the treatment of alcohol and drug addiction.

Affinity for the dopamine autoreceptor was established by a modification of the standard pharmacological test procedure of Seemen and Schaus, European Journal of Pharmacology 203: 105–109, 1991, wherein homogenized rat striatal brain tissue is incubated with [$^3$H]-quinpirole (Quin.) at various concentrations of test compound, filtered, washed and counted in a Betaplate scintillation counter.

High affinity for the dopamine $D_2$ receptor was established by the standard pharmacological test procedure of Fields, et al., Brain Res., 136, 5789 (1977) and Yamamura et al., ed., Neurotransmitter Receptor Binding, Raven Press, N.Y. (1978) wherein homogenized limbic brain tissue is incubated with [$^3$H]-spiperidone at various concentrations of test compound, filtered washed, and shaken with Hydrofluor scintillation cocktail (National Diagnostics) and counted in a Packard 460 CD scintillation counter.

The results of the evaluation with the compound of this invention made in Example V are given below.

| $IC_{50}$ (nM) $D_2$ Quin. | $IC_{50}$ (nM) $D_2$ Spiper | Ratio antagonist |
| --- | --- | --- |
| 0.57 ± 0.2 | 85.00 ± 0.0 | 149 |

These results indicate that this compound effects the synthesis of the neurotransmitter dopamine and thus is useful in the treatment of dopaminergic disorders such as schizophrenia, Parkinson's Disease, hyperprolactinemia, depression, Tourette's Syndrome, alcohol addiction, cocaine addiction, and addiction to analogous drugs.

What is claimed is:

1. A compound of formula VI

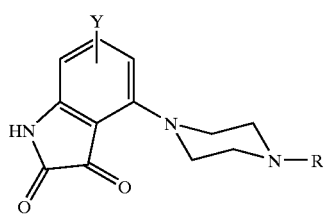

VI wherein Y represents hydrogen, methyl, methoxy, methylthio, or trifluoromethyl;
R represents $(CH_2)_n Ar$;
n is 0, 1 or 2; and
Ar represents phenyl or methoxyphenyl,
or pharmaceutically acceptable salts thereof.

2. The compound of claim 1 wherein Y is hydrogen, and R is benzyl.

3. The compound of claim 1 wherein R is benzyl.

4. A composition comprising a compound according to claim 1 and a pharmaceutically acceptable carrier.

5. A composition according to claim 4 wherein said compound is 4-(4-benzyl-piperazin-1-yl)-1H-indole-2,3-dione or a pharmaceutically acceptable salt thereof.

6. A compound of formula VII

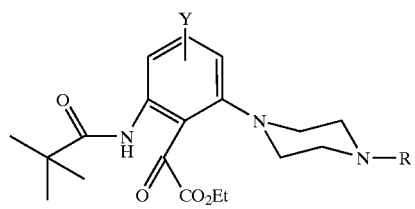

VII wherein Y represents hydrogen, methyl, methoxy, methylthio, or trifluoromethyl;
R represents hydrogen, $C_{1-3}$alkyl, or $(CH_2)_n Ar$;
n is 0, 1 or 2; and
Ar represents phenyl or methoxyphenyl.

7. The compound of claim 6 wherein Y is hydrogen and R is benzyl.

8. A process for making a compound of formula VI or pharmaceutically acceptable salts thereof

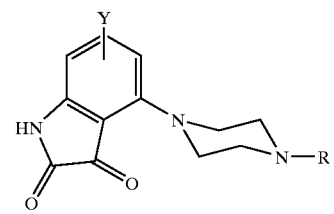

VI comprising acid catalyzed cyclization of a compound of formula VII

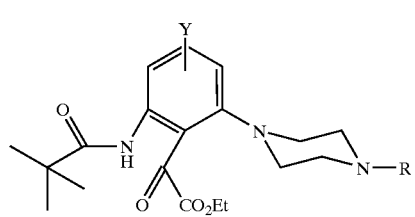

VII wherein Y represents hydrogen, methyl, methoxy, methylthio, or trifluoromethyl;
R represents hydrogen, $C_{1-3}$alkyl, or $(CH_2)_n Ar$;
n is 0, 1 or 2; and
Ar represents phenyl or methoxyphenyl.

9. A process for making 4-(4-benzyl-piperazin-1-yl)-1H-indole-2,3-dione comprising acid catalyzed cyclization of [2-(4-benzyl-piperazin-1-yl)-6-(2,2-dimethylpropionylamino)phenyl]-oxo-acetic acid ethyl ester.

10. A method for treating a disorder selected from the group consisting of schizophrenia, Parkinson's disease, hyperprolactinemia, depression, and Tourette's syndrome, in a mammal suffering from said disorder, comprising administering an effective amount of a compound according to claim 1.

11. A method according to claim 10 wherein said disorder is schizophrenia and said compound is 4-(4-benzyl-piperazin-1-yl)-1H-indole-2,3-dione or a pharmaceutically acceptable salt thereof.

* * * * *